United States Patent [19]

Hesse et al.

[11] 4,336,329
[45] Jun. 22, 1982

[54] METHOD AND APPARATUS FOR TREATMENT OF BIOLOGICAL SUBSTANCES, PARTICULARLY FOR CULTIVATION OF BIOLOGICAL CELLS AND TISSUES, OR OF MICROORGANISMS

[75] Inventors: Peter Hesse, Bruchköbel; Friedbert Schinle, Hanau am Main; Helmut Loscher, Nidderau, all of Fed. Rep. of Germany

[73] Assignee: W. C. Heraeus GmbH, Hanau am Main, Fed. Rep. of Germany

[21] Appl. No.: 160,230

[22] Filed: Jun. 17, 1980

[30] Foreign Application Priority Data

Jun. 18, 1979 [DE] Fed. Rep. of Germany ....... 2924446

[51] Int. Cl.³ .......................... C12M 1/36; C12Q 3/00
[52] U.S. Cl. ........................................ 435/3; 422/298; 435/289; 435/290; 435/809
[58] Field of Search ................. 236/2, 3; 422/26, 298; 435/3, 289, 290, 809

[56] References Cited

U.S. PATENT DOCUMENTS

| | | |
|---|---|---|
| 1,695,008 | 12/1928 | Christensen ......................... 435/809 |
| 1,902,625 | 3/1933 | Dunham ............................. 422/298 |
| 3,637,977 | 1/1972 | Folke ................................. 422/298 |
| 3,873,423 | 3/1975 | Munder et al. ....................... 435/3 |
| 3,929,584 | 12/1975 | Mansfield ............................ 435/3 |
| 3,941,662 | 3/1976 | Munder et al. ..................... 435/284 |
| 4,045,179 | 8/1977 | Bunce ................................ 236/3 |
| 4,090,921 | 5/1978 | Sawamura et al. ................. 435/809 |
| 4,142,940 | 3/1979 | Modolell et al. ................... 435/313 |
| 4,154,652 | 5/1979 | Sawamura et al. .................... 435/3 |
| 4,167,450 | 9/1979 | Chesbro et al. ....................... 435/3 |

FOREIGN PATENT DOCUMENTS

| | | |
|---|---|---|
| 7238351 | 2/1973 | Fed. Rep. of Germany . |
| 2541000 | 7/1977 | Fed. Rep. of Germany . |
| 2128744 | 3/1979 | Fed. Rep. of Germany . |

*Primary Examiner*—Peter A. Hruskoci
*Attorney, Agent, or Firm*—Frishauf, Holtz, Goodman & Woodward

[57] ABSTRACT

To establish predetermined humidity levels within a sterile treatment chamber, and maintain sterility, water, preferably deionized, is conducted to an evaporator outside of a container defining the treatment chamber, to be there heated to superheated steam, for example in the order of 300° C., and conducted to a bypass duct (1) in atmospheric communication with the treatment chamber (10), for mixing with the atmosphere within the treatment chamber. Preferably, the treatment chamber is surrounded by heat exchanger elements, such as electrical heating wires and/or cooling coils, the heaters being controlled to rapidly heat the treatment chamber to a temperature in the order of 180° C. during pauses of treatment for sterilizing the interior of the container, and/or maintaining temperature levels at a desired treatment level in operation. Additional gases to establish controlled atmospheres can be admitted to the interior of the treatment chamber, preferably after having passed through a heat exchanger for establishment of a desired temperature level.

32 Claims, 4 Drawing Figures

METHOD AND APPARATUS FOR TREATMENT OF BIOLOGICAL SUBSTANCES, PARTICULARLY FOR CULTIVATION OF BIOLOGICAL CELLS AND TISSUES, OR OF MICROORGANISMS

The present invention relates to treatment of biological materials, such as cells, tissues, microorganisms or the like, and more particularly to cultivation of such biological materials.

BACKGROUND AND PRIOR ART

Cells, tissues, microorganisms and other biological materials and substances, collectively and generally referred to hereinafter as "biological materials", frequently have to be treated for growing of cultures and the like. Some of these substances require sterilization before being subjected to treatment. Incubators and other containers have been provided in which predetermined temperature and humidity conditions are maintained. The gas atmosphere within the containers can also be controlled, for example by controlling the oxygen content or admitting other gases such as $CO_2$, nitrogen, pure oxygen, or the like. In one such apparatus, temperature and humidity are controlled and maintained at an essentially constant level by saturating gases or air admitted into the container with water vapor. To provide the necessary humidity, a water boat or vessel, or a sump, is placed in the container in which a predetermined water level is established.

It has been found that maintaining a vessel with water within the treatment area of the container or incubator, for example, in short the cultivation space, may introduce the danger of contamination by fungi or bacteria for the cultures to be treated due to the relatively high humidity within the cultivation space.

Reference is made to prior patents, and specifically U.S. Pat. No. 3,941,662, Div. of 3,873,423, which describes a process of the type to which the present invention relates; U.S. Pat. No. 4,142,940, and German Utility Model DE-GM No. 72 383 51 which, respectively, show incubating containers suitable for use with appliances and devices of the type to which the present invention relates.

THE INVENTION

It is an object to improve the known methods for treatment of biological materials by controlling the atmosphere wherein the container to approximate physiological conditions "in vivo" and, generally, to improve control over the incubation or growing process of the biological material.

Briefly, in accordance with a feature of the invention, sterilized water vapor, preferably derived from condensed steam, is introduced into the cultivation space. In accordance with a feature of the invention, steam is introduced into a bypass or separated area, there cooled, and admixed, for example by a circulating ventilator with the atmosphere within the controlled space. The space itself can be sealed, that is, closed gas and airtight, and, by being exposed to suitable heat exchangers, can be heated or cooled to provide any desired temperature therein. The biological material may be plant or animal or human tissues or cells, bacteria, or microorganisms in general.

The invention, thus, departs from the prior art by supplying the necessary humidity in the form of steam which is sterilized outside of the container or housing and derived from water supplied to an evaporator. The steam is then cooled and introduced into a bypass duct for eventual introduction into the treatment chamber; condensate can be removed by a pump or by gravity. The danger of contamination is substantially reduced. Undesired formation of condensation within the controlled space can also be further reduced by heating the jacket or wall surfaces of the chamber. The relative humidity no longer will approach that of about saturation but can be controlled in the wide range of from between/60% to 95%. The desired relative humidity can be obtained quickly. The atmospheric composition and the temperature of the treatment space likewise can be reached quickly, even after the door to the treatment chamber has been opened, for removal of treated substances and reintroduction of new ones, and then closed again. The treatment chamber itself can readily be sterilized in operating gaps, for example under an automatic control which, upon opening of the door, heats the interior space to a sterilizing temperature.

In accordance with a feature of the invention, a chamber is defined by a treatment cubicle, for example of essentially box-like construction, with a door capable of being closed in air and gas-tight manner, and having means to apply various gases thereto, such as, for example, carbon dioxide, air, oxygen, nitrogen or other gases. The jacket of the structure includes heating and cooling elements, such as electrical heaters or cooling coils, so that the interior thereof can be controlled to have a certain temperature. The steam which is supplied in order to insure a predetermined humidity is generated outside of the container in an evaporator, so that the steam being admitted will be sterilized, and then is cooled in a bypass section or a separate compartment within the cubicle structure.

The apparatus permits expansion of the utility thereof by improving the control and supervision of conditions within the treatment space or chamber. Various types of containers for the substances to be treated can be used, for example the foil-type containers described in U.S. Pat. No. 3,941,662, but also culture bottles as described, for example, in German Utility Model DE-GM No. 72 38 351. Dish or pot-like containers, as described in U.S. Pat. No. 4,142,940, may also be used.

DRAWINGS

Figure 4:
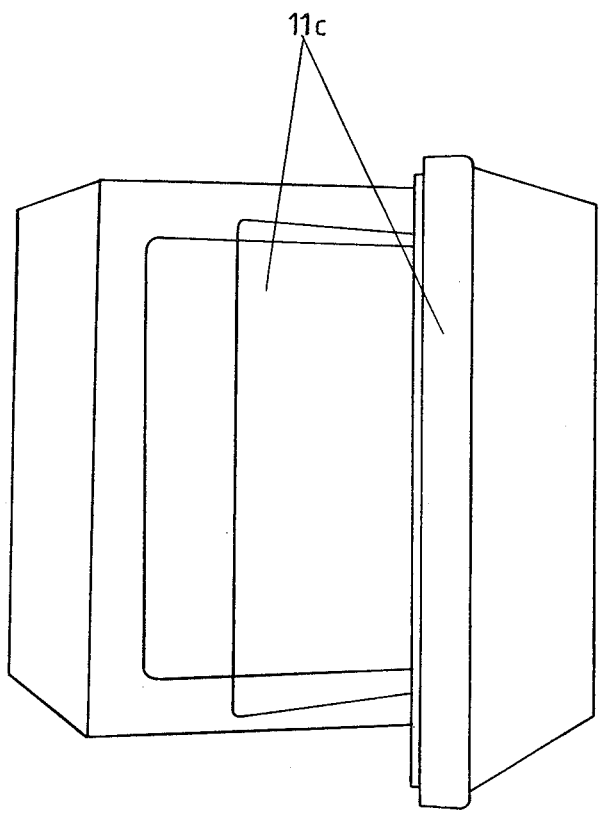

and FIG. 4 is a front view of the apparatus with inner and outer doors opened in rest position with gas valves closed and electrical circuitry interrupted.

Figure 1:
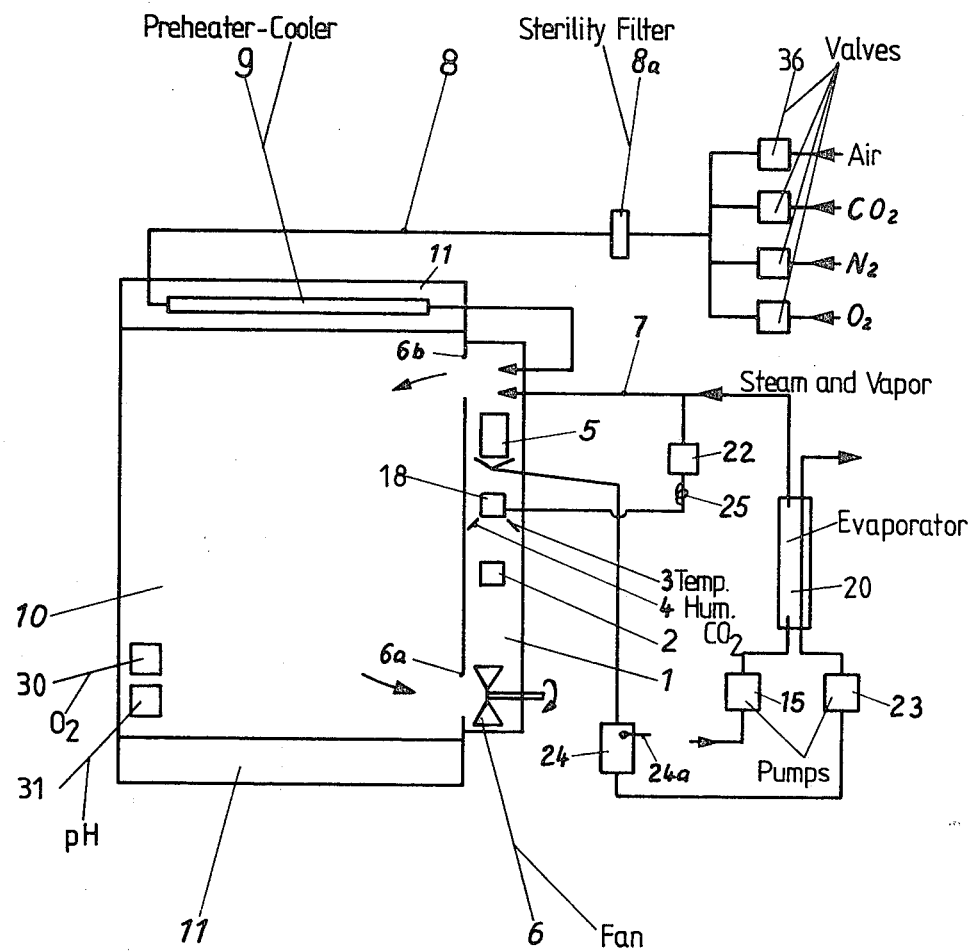
FIG. 1 is a highly schematic representation of the devices and appliances used and of the apparatus, to explain the method and schematically show the arrangement of the structure.

The container providing the controlled atmosphere is generally shown in FIG. 1 to define a cultivating space 10 in which an electronically controlled, biologically suitable atmosphere is maintained. The atmosphere may, for example, be so controlled that it approximates as closely as possible "in vivo" conditions. It is possible to change the composition of the atmosphere within wide limits, and particularly within the components of the mixture submitted thereto in gaseous form. The atmosphere may contain, besides oxygen or air, nitrogen, carbon dioxide and humidity or moisture vapor, within predetermined controlled limits. The temperature, relative humidity, and the controlled proportion of the gases permit, by use of the Henderson-Hasselbach relationship, also control of the pH values, by controlling the $CO_2$ contents of the gases. For some conditions, control of the pH is desirable.

A bypass channel or duct 1 (FIGS. 1, 3) is thermally coupled to the treatment space 10. Sensors to sense the conditions within the treatment space 10 are located in the bypass, such as a $CO_2$ sensor 2 to sense the $CO_2$ content, temperature sensor 3, humidity sensor 4; if desired, electrode 30 and a pH sensor 31 may also be located within the housing defining the space 10; the oxygen sensor 30 and the pH sensor 31 are preferably not located within the bypass but within the treatment space 10. The pH sensor may be so positioned that it can be introduced into liquid culture media. The interior of the treatment space may have a connecting plug 39 (FIG. 2) for connection of suitable cables to the sensors, which are only schematically illustrated and which may be of any commercially available construction. Plug 39 can also be used to supply electrical power to appliances and devices within the treatment space 10.

The treatment space 10 is subject to a controlled and monitored atmosphere, as desired, by supplying, respectively, gases from sources marked "AIR", $CO_2$, $N_2, O_2$". Controlled valves 36, which control the pressure and throughput, are located in advance of the connecting line 8 to the treatment chamber. A sterility filter 8a likewise is introduced in the connecting line. Of course, separate connecting lines may also be used. Connecting line 8 passes through a preheater or precooler 9, forming a heat exchanger and located within a double jacket 11 of the container or structure defining the space 10. The thus preheated or precooled gases, after having passed through the heat exchanger 9, are introduced into the bypass duct 1, to be there mixed with water vapor from the line 7. Water vapor from line 7 is obtained by superheating steam derived from water applied to an evaporator 20, so that the water is sterilized outside of the container or housing structure. The steam or vapor is then cooled in the temperature is brought down substantially, for example to +3° C., and introduced into the bypass duct of chamber 10 in the form of vapor.

Figure 2:
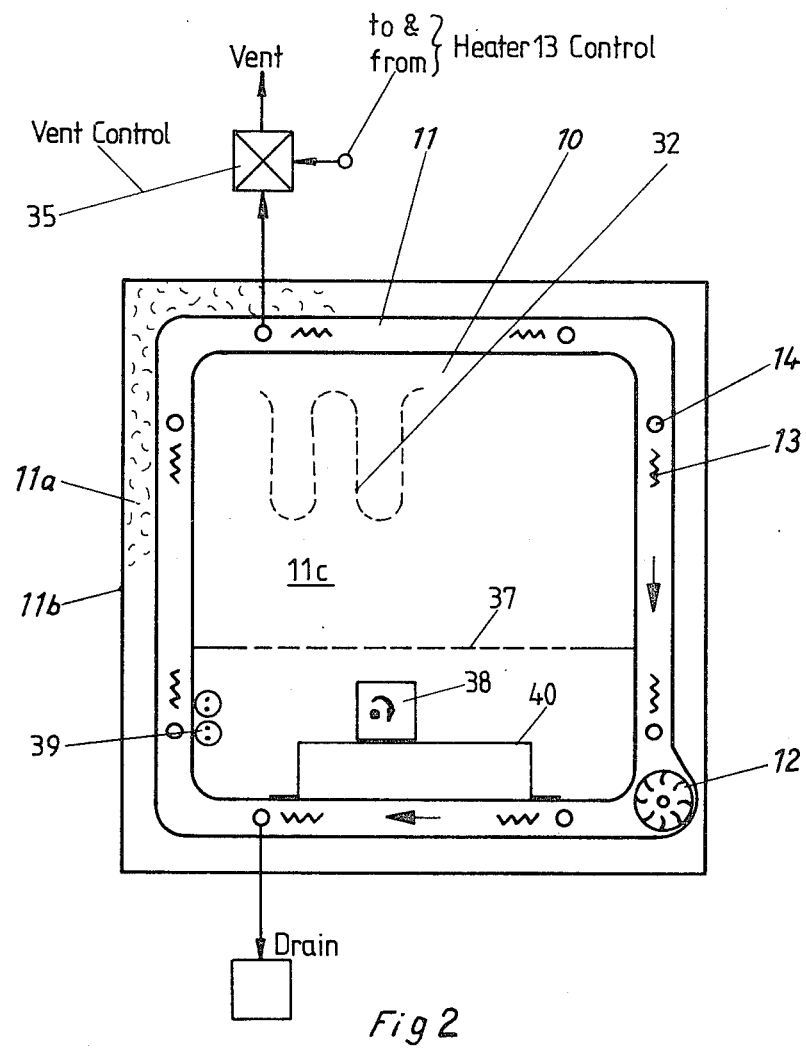
FIG. 2 is an end view of the treatment container, partly in section, and looked at from the rear with the rear cover removed, and further illustrating, highly schematically, one possible form of interior arrangement.

The container or housing structure is best seen in FIG. 2. The treatment space 10 is defined by a container 11 which is constructed as a double-jacketed, preferably essentially box-like structure, surrounded by a heat-insulating layer 11a which, at the outside thereof, is closed off by a vapor and watertight skin 11b, for example made of aluminum foil. Of course, further mechanical protective coverings may be provided. The foil 10 prevents ingress from air from the outside and prevents accumulation of dampness within the insulating material when the space 10 within the structure is operated under cooled conditions. Heaters 32 are located along the back walls of the container and also on the door 11c to prevent formation of condensation thereof. It is also sometimes desirable to locate such heaters on the top wall or ceiling of the container and on the door 11c thereof. The door itself is preferably made in double construction, having an inner glass wall and an outer opaque door which, if desired, can be opened separately to permit visual observation, while excluding ambient light from the interior, if desired.

The atmosphere within the space between the double walls of jacket 11 is constantly circulating; a blower 12, for example of the turbine wheel type (see FIG. 2) is located in a corner within the dual walls of the structure 11. Preferably, the blower extends throughout the depth of the structure or, if located transversely with respect thereto, across its width. The double wall 11 has heat exchange elements located in heat transfer relation with respect thereto to provide a controlled-temperature wall surrounding to the space 10. Heater elements 13 and cooling coils 14 are positioned in heat transfer relationship with respect to the inner one of the double walls forming the container 11. Preferably, the heater elements 13 and the cooling channels 14 are symmetrically located, that is, are uniformly distributed over the entire circumference of the double wall jacket—see FIG. 2. The double wall jacket 11 thus can provide excellent uniformity of temperature throughout its extent, and thus provide uniform temperature within the space 10 so that, in spite of the high humidity therein, the dew point is not exceeded.

Figure 3:
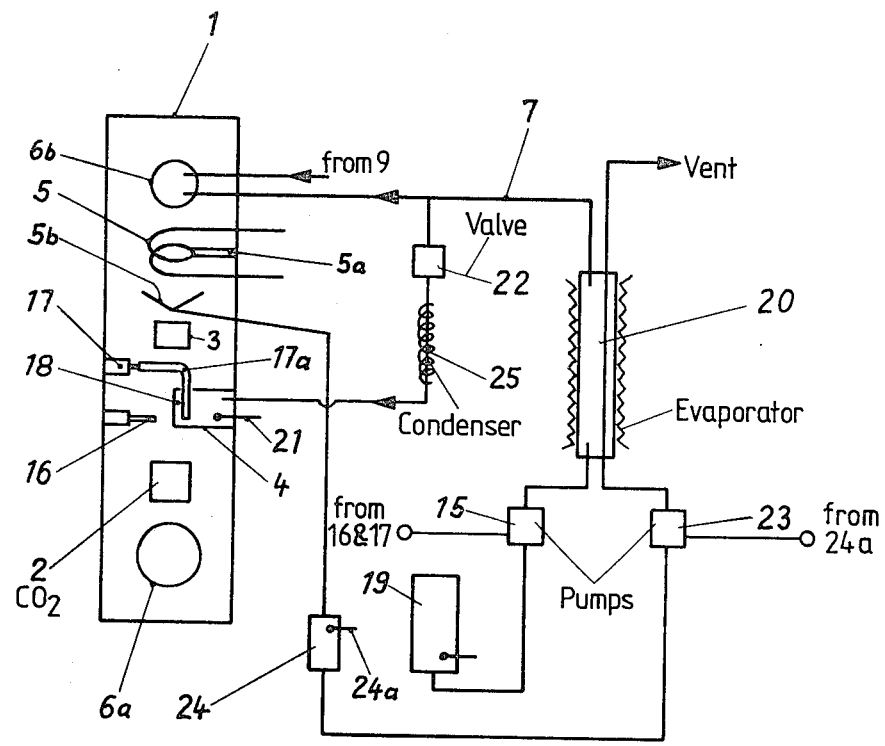
FIG. 3 is a highly schematic representation of the control and monitoring and supervisory arrangement to control the atmosphere within the treatment space of the treatment container illustrated in FIG. 2, partly repeating the elements shown in FIG. 1, and illustrating the same to substantially enlarged scale.

Humidity is controlled in a control loop individual thereto. The control parameter is derived from a psychrometer connected over control lines to a pump 15 (see FIG. 3) which takes water, preferably deionized water, from the supply container 19 and supplies the evaporator 30. The water is evaporated to steam in the evaporator 20 and superheated at a temperature of above 100° C. to, for example and preferably, 300° C. for sterilization. The superheated steam is supplied to the bypass duct 1 through line 7 where, in its passage, it cools, for subsequent supply to the utilization space or chamber 10. The psychrometer is formed by the assembly of a dry-bulb thermometer 16 and a wet-bulb thermometer 17, for example a resistance thermometer. The wet-bulb thermometer includes a wick 17a which dips into a suction cup 18, all located within the bypass 1, as schematically shown in FIG. 3.

The psychrometer is preferably located at a constriction of the duct 1 formed, for example, by the cup 18 itself (FIG. 3) so that the sensor and at least the web-bulb thermometer is exposed to an optimum gas flow of the gaseous medium being supplied by the blower 12 (FIG. 2). The $CO_2$ sensor 2 to determine the concentration of $CO_2$ gas is likewise located in the bypass duct 1. Temperature sensor 3 senses the temperature of the gas being circulated by the blower 12.

$CO_2$ control is effected by its own control loop. The $CO_2$ sensor may, for example, be a hot conductor measuring cell. Such a cell includes four platinum resistors, connected in a bridge circuit, and retained within an isothermal housing at a predetermined temperature, for example at about 130° C. Two of the resistors are located in chambers in which a reference gas, for example air, is provided; the other two are exposed to the atmosphere to be tested. If the heat conductivity in the test chamber changes, differential cooling of the measuring resistors will provide an electrical output representative of the $CO_2$ proportion in the test atmosphere. This sensing signal is directly applied to a control unit, for example a controller which, in turn, operates the respective valve 36 controlling $CO_2$ supply, as well known in the gas control field.

The preferred sensor for temperature control is a platinum resistant element, such as sensor Pt100, connected to a controller having proportional-integrating-differentiating characteristics. A time-temperature integrator may be connected to the sensor, as well as a programming switch which controls timed programs of various temperature conditions to obtain within the chamber 10.

The trap 5 has a defrost unit 5a associated therewith, and further includes a collecting trough 5b. Condensate water is conducted from the trough 5b to a supply container 24 having a level sensor 24a therein; such a sensor, in its simplest form, is a float. If the float rises above a predetermined level, the vessel 24 is emptied by starting of a pump 23 which circulates the resulting water through the evaporator 20, for example for venting to the outside atmosphere, as schematically illustrated in FIG. 3.

The evaporator 20, preferably, is a tubular structure with an electric heater surrounding the furnace jacket, for heating of the contents passing through the furnace to a predetermined temperature. The humidity control system further includes a condensation device, such as a tubing coil 25 and a magnetic valve 22, connected to the steam line 7 from the evaporator to the bypass 1 to introduce condensate of part of the steam from evaporator 20 into suction cup 18 for which 17a of the wet bulb thermometer 17 to avoid contamination of the atmosphere circulating in chamber 10 and bypass 1, which otherwise might occur due to bacteria in water.

Method of treatment and operation of the treating system:

After engaging a main switch (not shown), the heater elements 13 (FIG. 2) surrounding the inner walls of the housing are connected. The blower 12 (FIG. 2) is started. Temperature sensor 3 will sense the temperature of the atmosphere within the housing and, selectively, control the heater elements 13 or admission of cooling fluid to cooling coils 14. Such temperature control is standard and well known. The flow of gases within the double wall of the jacket 11 is controlled to effect the appropriate temperature within the chamber 11. The circulating fan 6 likewise is started in order to insure uniformity of temperature within the chamber 10. Circulating fan 6 likewise passes the atmosphere within the chamber 10 into the bypass duct 1. The bypass duct 1, preferably, is located in intimate thermal contact with the chamber 10 and, for ease of access to the chamber 10, positioned at its rear wall.

The cup or container 18 which supplies water to the wet-bulb thermometer 17 is originally empty. The wick 17a of the wet-bulb thermometer thus is dry and, likewise, the level sensor 21 within the cup 18 (FIG. 3) provides an "empty" signal to the humidity control loop. Pump 15 is controlled to start as soon as the evaporator 20 is heated to sufficient temperature to evaporate any liquid put therethrough. Starting of pump 15 is controlled by an interlock between the evaporator 20 and the pump, in accordance with well known technology. After the evaporator 20 has reached evaporating temperature, and pump 15 has started, the pump 15 is controlled by the psychrometer formed by the wet-bulb and dry-bulb thermometers 17, 16. The evaporator 20 remains continuously energized. Pump 23 is started under control of the level switch 24a for a short period of time if the level switch 24a provides a signal in order to empty the container 24, when required, that is, when sufficient condensed and evaporated water has collected in the trough 5b and then in the vessel 24.

The desired temperature in the treatment space 10 is maintained by relative operation of the heaters 13 and of the cooling coils 14. For some operations, the temperature within the space 10 should be, for example, about +3° C. Cooling is then effected by supplying a cooling fluid through the coils 14 positioned within the double walls of the housing jacket 11. Suitable cooling fluids are water or brine, preferably connected in a closed cooling circuit. The cooling circuit is controlled by a separate thermostat—not shown—in accordance with a demand setting applied thereto which is below room temperature. An interlock is provided to prevent simultaneous operation of the heater elements 13 and the cooling coils 14, as well known in connection with temperature control and air-conditioning of confined spaces.

Cooling, and the cooling loop or circuit, is independent—except for mutual interlocks—of heating and the heating circuit for the space 10, and can be independently controlled. Preferably, the door 11c likewise includes heating elements and it may, also, include cooling coils connected into the cooling circuit by flexible pipes.

The mixture of the atmosphere within the chamber 10 is controlled by controlling supply from the respective supply sources. The supply sources, for example bottles retaining the respective gases in compressed form, are connected to valves 36, preferably magnetically controlled valves. The humidity within the space 10 is controlled by controlling the admission of water vapor which has been sterilized by first bringing it through a superheated steam phase, drying and then cooling the resulting steam to the desired temperature. $CO_2$ control and air control are obtained by suitable setting of the valves 36.

Extremely fine control of the composition of the atmosphere within the space 10 can be obtained by also controlling the oxygen pressure ($pO_2$) therein. Oxygen pressure can be sensed by utilizing a Clark electrode in combination with an oxygen permeable membrane which is impermeable to liquids. The electrode utilizes a platinum cathode and a silver anode, within an electrolyte of 0.3 mol potassium chloride solution. The electrode is separated by the membrane from the surrounding atmosphere in space 10. Oxygen within the atmosphere will diffuse through the membrane and is reduced at the platinum-cathode. Applying a polarization voltage to the electrodes, for example of a few hundred millivolts, permits measuring the reduction current. This current is directly proportional to the partial pressure of the oxygen within the atmosphere in chamber or space 10.

When the predetermined oxygen concentration within the chamber 10 has been reached, the sensor provides an output signal to the respective valve 36 for oxygen to close to oxygen supply valve.

An interlock is preferably provided interlocking the door 11c and the respective valves 36. As soon as the door is opened, supply of any gases is automatically stopped.

Oxygen partial pressure can be set and maintained to be above the partial pressure in air, that is, to be above 21%. Additional oxygen can be supplied by suitable control of admission via the respective valve 36. Oxygen partial pressure below that of the air, that is, under 21%, is controlled by admitting additional nitrogen into the space or chamber 10. Selective admission of oxygen and nitrogen can be controlled, automatically, by processing the signals from the Clark electrodes which measure the respective oxygen concentration.

Gas mixtures having a concentration of $CO_2$ and $O_2$, together more than 95% by volume, should preferably not be selected due to the high use of gas. The door 11c includes not only an interlock with respect to the heaters, but also with the valves 36 to interrupt supply of gas as soon as the door is opened, and to maintain the gas supply interrupted under all conditions so long as the door remains open. The valves 36 preferably also include a manual override to permit manual control of the respective gases as well as automatic control, if desired.

Some treatment processes of some materials release $CO_2$. If this is the case, and to maintain an appropriate $CO_2$ concentration within the atmosphere, a separately connectable pump or pressure supply of air, oxygen or nitrogen to the atmosphere in chamber 10 is desirable. Control of the supply can be effected by the respective valves 36, in order to prevent rise of the $CO_2$ concentration within the space or chamber 10 to an undesired level. Upon opening of the door 11c, and removal of the treated materials, the chamber of course is automatically vented. Upon reclosing of the door, the controlled parameters rapidly reach the desired values.

The pH value can be maintained at a desired level by a separate pH controller 31. A typical sensor comprises an electrode with a buffer solution in a referenced culture vessel, for example including a single-rod measuring arrangement. Reference vessels of this type are known. Buffer solutions for pH control which are particularly suitable include a medium comprising bicarbonate or containing bicarbonate. This medium is regenerated from time to time, and has been found suitable.

Treatment can be carried out under highly sterile conditions by proceeding as explained. The interior walls of the housing defining the chamber 10 preferably are made of stainless steel or may include a copper lining if there is particularly high danger of contamination.

The system is readily capable of hot-sterilizing itself during pauses in use, so that the chamber is always immediately ready when a main switch is started. Sterilizing, for example, is effected by opening a vent control valve 35 (FIG. 2) located at an upper point of the cooling coils 14. The cooling liquid then runs, by gravity, back into the drain or sump therefor. When the cooling liquid has drained, the heater 13 and, preferably, also the ventilating fan 6 are started. When the thermostat 3 senses a temperature of about 180° C., or higher, as desired, within the chamber 13, heating energy can be reduced to maintain this temperature for a sterilization time, for example, under control of a timer—as well known—for a period of between one and several hours, depending on the types of cultures which were within the chamber. Upon elapse of time, the thermostat and heat energy are disconnected. Preferably, the blower 12 is also energized to operate, so that the temperature within the double walls of the housing 11 is essentially uniform thereover, and the fan 6 insures uniformity of temperature within the chamber or space 10. Heat, thus is essentially uniformly distributed throughout. This sterilizing step permits expansion of use of the apparatus and to extend it to cultivate materials of different kinds. Other known sterilization methods can be reduced or can be eliminated. The heat, of course, is applied not only to the chamber 10 but also to the region within the bypass 1 so that the elements therein are likewise sterilized.

Although not necessary, but in a preferred form, the bypass 1 can be isolated from the interior of the chamber by providing externally or internally controlled doors 6a, 6b which connect air flow communication between the chamber 10 and the bypass 1. Preferably, the doors are so arranged to also function as gas flow directing baffles when open—see FIG. 1.

The space or chamber 10 forming the treatment space preferably is so arranged that it can accept racks, trays, or holders of various kinds on which cultivating dishes, trays, bottles or the like can be placed. Typical cultivation holders are semi-permeable foil containers of different shape and form, Petri dishes, bottles, titration plates, or other holders and supports as customarily used in the biological and biochemical fields.

The space or chamber 10 can be an undivided, entire single space, through which treatment processes can be observed if the door 11c contains a glass unit. The chamber can also be subdivided, for example by a divider or shelf schematically indicated at 37. Other subdivisions, for example extending vertically to divide the chamber into several vertical subchambers, can be used. Using culture bottles, such as narrow-neck bottles, permits use of rotating or tipping apparatus, schematically indicated at 38. Holders or racks 40, and rotating, rocking or other movable apparatus, appliances and devices can be used, and the plug 39 can supply not only a connection for sensing elements, but also for electrical power, for example for an electrical motor to drive a rotary or rocking device 38. Such different types of holders, both stationary and movable, are known and form articles of commerce.

Various changes and modifications may be made, and features described in connection with any one of the embodiments may be used with any of the others, within the scope of the inventive concept.

We claim:
1. Method of treating biological materials comprising positioning the materials in a container;
providing a housing structure (11) defining a treatment chamber (10) and a bypass duct (1);
introducing at least one container with the materials therein into the chamber;
maintaining the temperature within the chamber at a predetermined temperature level;
selectively introducing gas components into the chamber; humidifying the atmosphere within the chamber to provide a predetermined humidity level within the chamber,
wherein the step of providing the predetermined humidity level comprises
generating sterile water vapor;
cooling the water vapor to a desired temperature;
controllably introducing the cooled water vapor into the bypass duct (1);
mixing the cooled water vapor with the gas component;
and circulating the atmosphere within the treatment chamber and the bypass duct to provide for uniformity of atmosphere and gaseous and vapor mixtures within the chamber and the bypass duct, and mixing of the components of the atmosphere and the vapor by turbulence.

2. Method according to claim 1, wherein the step of generating the sterile vapor comprises heating water to above the boiling point and generating steam;
superheating the steam;
and cooling the steam.

3. Method according to claim 2, wherein the step of heating the water comprises heating the steam to sterilizing temperature and thereby drying the steam.

4. Method according to claim 1, further including the step of sterilizating the interior of the chamber and the bypass by heating the atmosphere therein prior to introduction of the materials therein to a sterilizing temperature.

5. Method according to claim 1, wherein
wherein the steps of introducing the gas components into the chamber and introducing the water vapor into the chamber comprises mixing the gas components and the water vapor before admitting the mixture into the treatment chamber;
and the step of removing the condensate arising upon cooling of the steam is carried out in said bypass duct.

6. Method according to claim 1,
further including the step of controlling the temperature of the interior of the treatment chamber and said bypass duct by circulating a fluid of controlled temperature within a surrounding jacket.

7. Method according to claim 6, wherein the chamber is surrounded by a jacket having cooling coils retaining a cooling fluid therein;
further including the step of draining the cooling fluid from the cooling coils prior to heating the interior of the chamber to a sterilizing temperature.

8. Method according to claim 6, wherein the step of controlling the temperature level of the atmosphere in the chamber comprises the step of reducing the temperature thereof to a level within the range of about 5° C. and 50° C.

9. Method according to claim 8, wherein the temperature reduction step comprises reducing the temperature of the steam to a level of between 20° C. and 37° C.

10. Apparatus for treatment of biological materials comprising
a housing (11) defining a chamber (1, 10) therein and having
a door (11c) selectively closing the chamber in gas-tight manner; subdividing means in said housing for dividing said chamber into a main treatment chamber (10) and a bypass (1), said bypass being in atmospheric communication with the main treatment chamber;
humidity sensing means (4, 16, 17, 17a) positioned within the bypass;
gas supply means (AIR, $CO_2$, $N_2$, $O_2$) connected to the housing for supplying a predetermined gas under controlled conditions;
temperature control means (13, 14) in thermal transfer relation with the inner walls of the housing surrounding the chamber for maintaining the chamber at a predetermined temperature;
an evaporator (20) positioned outside of the housing and furnishing a supply of sterilized steam;
means (7) for cooling and conducting said steam into the chamber;
means (5) for cooling the steam to obtain sterilized water vapor positioned within said bypass (1)
condensate collection means (5b) positioned within the bypass for conducting condensate to the outside of said housing;
and means (6b) for supplying said sterlized water vapor to the space defining the chamber.

11. Apparatus according to claim 10, further including water supply means (19), and means (15) for controllably conducting water from said water supply means (19) to the evaporator (20), said controllable water conducting means being controlled by the humidity sensing means for selectively supplying water to the evaporator to maintain the humidity within the treatment chamber at a predetermined level.

12. Apparatus according to claim 11, further including gas circulating means for circulating the gas components forming the atmosphere within the chamber through the main treatment chamber and the bypass, said gas circulating means providing for uniformity of composition of the atmosphere within the main treatment chamber and for turbulence of the components thereof as they pass through the bypass to provide for intimate mixing of the components.

13. Apparatus according to claim 10, wherein the housing has a double wall, the outer wall thereof being heat-insulated and being gas and vapor-tight;
the temperature control means includes heating means and cooling means forming a heat exchanger positioned within the double walls of the housing, said double walls forming, therebetween, open spaces permitting circulation of fluid therethrough;
and forced circulating means (12) are provided located in the space between said double walls to circulate said fluid and provide for uniformity of heat transfer to the inner walls of the housing surrounding said chamber essentially throughout the extent thereof.

14. Apparatus according to claim 13, wherein the fluid within the space defined by the double walls is air.

15. Apparatus according to claim 10, further including heater elements located in heat transfer relationship with at least portions of the inner walls of the housing and heatable to prevent formation of condensation thereon.

16. Apparatus according to claim 15, wherein the heater elements are positioned, in part, in heat transfer relation with the door.

17. Apparatus according to claim 10, wherein the housing (11) comprises a double-wall structure having heat insulation at the outside thereof;
and a preheater-cooler forming a heat exchange element (9) is positioned within the double walls forming the housing and of the treatment chamber in heat transfer relation with the gas supply means at a location immediately in advance of admission of the gases into the chamber (10) defining the housing to selectively preheat or precool the gases being supplied to the chamber and to provide for said controlled conditions.

18. Apparatus according to claim 10, including
forced gas circulation means (6) positioned in the bypass for circulating the gas components forming the atmosphere within the chamber through the main treatment chamber and the bypass, generating turbulence, and intimately mixing the gas components and the sterilized water vapor.

19. Apparatus according to claim 18, wherein the means (5) for cooling treatment atmosphere are located in the bypass.

20. Apparatus according to claim 18, further including atmospheric condition sensing means (2, 3, 4) positioned within said bypass.

21. Apparatus according to claim 20, wherein the temperature control means (13, 14) includes heating means for heating both the treatment chamber and the bypass;

said heating means being capable of heating the treatment chamber and the bypass to a temperature in the order of about 180° C. to sterilize the entire chamber.

22. Apparatus according to claim 21, wherein the temperature control means includes cooling coils retaining a cooling fluid;

and means (35) connected to and interlocked with the heating means to drain cooling fluid from the cooling coils when the heating means are energized to heat the interior of the chamber to a sterilizing temperature.

23. Apparatus according to claim 10, further including a sterility filter (8g) connected downstream in the gas supply means and in advance of the chamber to sterilize gases from the gas supply means.

24. Apparatus according to claim 10, wherein the evaporator (20) is capable of heating water supplied thereto to steam at a sterilizing temperature;

and the cooling means is connected to receive the steam and provide water vapor at a lower temperature level into said chamber.

25. Apparatus according to claim 24, wherein said range is between about 20° C. and 37° C.

26. Apparatus according to claim 10, wherein said evaporator is a superheater for superheating water supplied thereto to dry steam at sterilizing temperature to provide sterilized steam to said cooling means (5) connected thereto and with the chamber.

27. Apparatus according to claim 10, wherein said door (11c) is a double door having an inner glass portion and an outer heatable opaque portion.

28. Apparatus according to claim 10, further including subdivision means (37) subdividing the main treatment chamber (10) into compartments, and support means 40 located within the respective compartments to support at least one of:

dishes, containers, plates;

for the biological materials therein.

29. Apparatus according to claim 10, further comprising semi-permeable containers for the biological materials within said main treatment chamber (10).

30. Apparatus according to claim 10, further comprising dish containers for the biological materials within said main treatment chamber (10).

31. Apparatus according to claim 10, further including driven movable holder means (38) positioned within said main treatment chamber (10) to hold and retain said biological materials.

32. Apparatus according to claim 10, further including electrical connection means (39) positioned within said main treatment chamber (10) to permit attachment of electrical connections to electrical apparatus (30, 31, 38) therein.

* * * * *